United States Patent

Gacon-Camoz et al.

[11] Patent Number: 5,874,654
[45] Date of Patent: Feb. 23, 1999

[54] PURIFICATION OF MIXTURES OF NITROAROMATIC COMPOUNDS BY REMOVING NITROCRESOLS THEREFROM

[75] Inventors: Antoinette Gacon-Camoz, Saint Priest; Pascal Metivier, Foy Les Lyon, both of France

[73] Assignee: Rhone Poulenc Chimie, Cedex, France

[21] Appl. No.: 934,115

[22] Filed: Sep. 19, 1997

Related U.S. Application Data

[63] Continuation of Ser. No. 343,966, Nov. 18, 1994, abandoned.

[30] Foreign Application Priority Data

Nov. 19, 1993 [FR] France .................................. 93 13823

[51] Int. Cl.$^6$ ................................................. C07C 201/16
[52] U.S. Cl. .................... 568/934; 568/705; 568/706; 568/708; 568/711; 568/712; 568/713; 568/927; 568/932; 568/935
[58] Field of Search .................... 568/706, 708, 568/711, 705, 712, 713, 927, 932, 934, 935

[56] References Cited

U.S. PATENT DOCUMENTS

| | | | |
|---|---|---|---|
| 3,894,096 | 7/1975 | Whitten | 568/708 |
| 3,917,719 | 11/1975 | Baldwin et al. | 568/708 |
| 3,980,717 | 9/1976 | Subluskey | 568/708 |
| 4,482,769 | 11/1984 | Toseland et al. | 568/934 |
| 4,604,214 | 8/1986 | Carr et al. | 210/759 |

FOREIGN PATENT DOCUMENTS

| | | | |
|---|---|---|---|
| 498947 | 7/1917 | France . | |
| 793486 | 4/1958 | United Kingdom | 568/708 |

*Primary Examiner*—Peter O'Sullivan
*Attorney, Agent, or Firm*—Burns, Doane, Swecker & Mathis, L.L.P.

[57] ABSTRACT

Environmentally-polluting nitrocresol values are removed from admixtures of nitroaromatic compounds comprised thereof, notably the media of nitration of aromatic compounds by reacting same with aqueous $HNO_3/H_2SO_4$, by first intimately contacting such nitroaromatic compound admixtures with an oxidizing agent comprising hydrogen peroxide, javelle water, or mixture thereof, and thereafter with a neutralizing agent; the nitroaromatic aromatic compounds thus purified are conveniently catalytically hydrogenated into aromatic amines.

18 Claims, No Drawings

PURIFICATION OF MIXTURES OF NITROAROMATIC COMPOUNDS BY REMOVING NITROCRESOLS THEREFROM

This application is a continuation of application Ser. No. 08/343,966, filed Nov. 18, 1994, now abandoned.

BACKGROUND OF THE INVENTION

1. Field of the Invention

The present invention relates to the purification of admixtures of nitroaromatic compounds produced via the nitration of aromatic compounds using nitric acid in the presence of sulfuric acid.

This invention especially relates to the removal of nitro-substituted cresols from admixtures of nitroaromatic compounds comprised thereof.

2. Description of the Prior Art

Nitroaromatic compounds, in particular aromatic compounds containing two nitro groups, are conventionally prepared via a two-step process. In the first step, the aromatic reactants are contacted with a mixture of nitric and sulfuric acids. The reaction mixture is then decanted and, in a second step, the organic phase containing the mononitrated aromatic compounds is contacted with a nitric acid/sulfuric acid mixture to produce the corresponding aromatic compounds which are substituted with two nitro groups.

The mixture from the second operation, however, contains objectionable byproducts, in particular cresols, especially those which are substituted with three nitro groups (hereinafter designated the "nitrocresols").

These nitrocresol byproducts must be separated from the nitroaromatic compounds before the latter can be subjected to any further reactions. In a process for the preparation of aromatic amines from the nitroaromatic compounds indicated above, for example, the nitrocresols are known to poison the catalysts employed for the reduction of the nitro groups into amine groups.

One known technique for separating the nitrocresols from the nitroaromatic compounds is to treat said mixture with a base and with water, whether simultaneously or successively, to transform the nitrocresols into salts, and to then separate out the organic phase, which principally contains nitroaromatic compounds, from the aqueous phase which contains the salts of the nitrocresols.

The difficulty with this particular technique is in the fact that the aqueous effluent contains amounts of nitrocresol salts which are too large and exhibit a very high chemical oxygen demand. As a result, effluents containing such salts cannot be discharged untreated to waste.

It is thus necessary to chemically or biochemically treat such effluents to reduce the amount of nitrocresol salts discharged, or to incinerate same. This, of course, significantly adds to the cost of the operation.

SUMMARY OF THE INVENTION

Accordingly, a major object of the present invention is the provision of an improved process for the removal of nitrocresol values from nitroaromatic compound admixtures thereof.

Another object of the present invention is the provision of an improved technique for reducing the total amount of nitrocresols present in discharge effluents comprised thereof, to an amount which is comparable to that obtained using known effluent treatments.

Yet another object of this invention is the provision of a simplified such process/technique that eliminates one step of the prior art and which is also more economical in respect of time and cost.

Briefly, the present invention features a process for the elimination or removal of nitrocresols contained in admixtures of nitroaromatic compounds comprised thereof, such admixtures having been prepared via nitration of aromatic compounds by means of nitric acid in the presence of sulfuric acid, and comprising contacting these admixtures with an oxidizing agent selected from hydrogen peroxide or javelle water, or a mixture thereof, and with a neutralizing agent.

DETAILED DESCRIPTION OF BEST MODE AND PREFERRED EMBODIMENTS OF THE INVENTION

More particularly according to the present invention, it will be seen that the subject purification treatment is not carried out on the aqueous effluent, as in the prior art, but on the reaction medium itself. By the term "reaction medium" is intended a mixture containing nitroaromatic compounds as a major fraction thereof, the nitrocresols being present as impurities therein, i.e., at a level on the order of one thousand parts per million.

As a result, subsequent (chemical or biochemical) treatment of the effluent is not required as regards the nitrocresols. Indeed, simple decantation of the reaction medium after treatment in accordance with the invention, followed by separating the resulting aqueous and organic phases, constitutes a sufficient treatment vis-a-vis the nitrocresols. It too will be appreciated, however, that other conventional effluent treatments could also be carried out prior to the discharge thereof.

It has also, surprisingly, now been determined that the total yield of the reaction which produces the nitroaromatic compounds is not adversely affected by the purification according to the invention. Taking account of the fact that traditional practice entails treating the aqueous phase after removal of the nitroaromatic compounds to eliminate the nitrocresols present, it was unexpected that the nitrocresols could be removed while still admixed with the nitroaromatic compounds formed. Indeed, while it would have been expected that such a destructive treatment would not be selective and would, therefore, effect destruction of a not insubstantial fraction of the nitroaromatic compounds present, exactly the contrary in fact occurs. More particularly, it has been determined that the treatment according to the invention provides the same total yield of nitroaromatic compounds as the prior art processes. Stated differently, no additional loss of nitroaromatic compounds is observed according to the process of the invention, compared with the prior art processes.

As indicated above, the present invention features a process for the elimination or removal of nitrocresols contained in admixtures which also comprise nitroaromatic compounds, such admixtures having been produced via nitration of aromatic compounds by means of nitric acid, in the presence of sulfuric acid.

The process of the invention thus comprises contacting said admixtures with an oxidizing agent, notably hydrogen peroxide, or javelle water ("eau de Javel," an aqueous bleaching solution of alkali metal, notably sodium hypochlorite), or a mixture thereof.

In a preferred embodiment of the invention, the oxidizing agent is hydrogen peroxide.

The amount of oxidizing agent which is added, expressed in moles, is at least equal to the number of moles of nitrocresol compounds present in the medium.

Advantageously, the process of the invention is carried out using a very large excess of oxidizing agent, with respect to the amount of nitrocresols present in the mixture to be treated.

Preferably, the number of moles of oxidizing agent employed in the subject process ranges from 15 to 1,000 moles per mole of nitrocresols, more preferably from 15 to 500 moles per mole of nitrocresols.

The oxidizing agent can be employed in its pure form or diluted in any appropriate solvent, preferably water.

When using the oxidizing agent in a diluted form, any concentration thereof may be employed. However, for kinetic and economic reasons, the concentration of said agent in the solution preferably ranges from 5% to 50% by weight.

The second reagent required to carry out the process of the invention comprises a neutralizing agent. By the term "neutralizing agent" is intended any compound which transforms the nitrocresols contained in the mixture into water soluble salts thereof.

Preferably, the neutralizing agent is selected from among the alkali or alkaline earth metal hydroxides, carbonates or bicarbonates, and mixtures thereof.

In a preferred embodiment of the invention, the neutralizing agent is an alkali metal hydroxide. Sodium hydroxide and potassium hydroxide are particularly suitable neutralizing agents for the process of this invention.

Said agent may also be employed either in its pure form or diluted in any appropriate solvent, preferably water.

When the neutralizing agent is used in a diluted form, the concentration of such agent can vary over a wide range. Said concentration preferably ranges from 5% to 50% by weight.

The amount of neutralizing agent employed in the process of the invention is such that the pH of the aqueous phase ranges from 1 to 9. It should be appreciated, however, that the process can be carried out under conditions wherein the pH of the aqueous phase is outside the range indicated.

The mixture to be purified may also contain a cosolvent for the nitroaromatic compounds produced, for example $C_6$–$C_{10}$ aromatic compounds, which may be substituted with hydrocarbon radicals and/or halogenated. Exemplary thereof are toluene, cumene and chlorobenzene.

In a first embodiment, the mixture resulting from the reaction of the aromatic compounds with the nitric acid in the presence of sulfuric acid is separated out in a decantation step. The aqueous phase, principally comprising the mixture of nitric and sulfuric acids, is separated from the organic phase containing the nitroaromatic compounds and the nitrocresols. The organic phase is then treated in accordance with the present invention.

In a second embodiment, the mixture emanating from the nitroaromatic compound production reaction, preferably after conducting the decantation/separation cycle described above, is washed with water, to eliminate residual acids.

This operation is carried out, as is usual, with stirring at a temperature of from 20° C. to 90° C. and for a period of time of from several minutes to two hours.

The mixture is then decanted and the organic phase, containing the nitroaromatic compounds to be purified, is separated from the aqueous phase.

It will be appreciated that the second embodiment can be repeated one or more times.

The mixture to be purified and the two agents described above are contacted in known fashion.

For example, the oxidizing agent can be contacted with said mixture, followed by the neutralizing agent, or vice versa. Simultaneous introduction of the two agents can also be carried out.

In this event, the two agents can be introduced into the reaction medium as a mixture, or in two separate feedstreams.

Preferably, the agents are introduced into the mixture to be purified, although the opposite is also within the scope of the invention, whatever the mode of introduction (simultaneous or successive) is selected for the agents.

The contacting is preferably carried out with stirring.

The temperature during the operation advantageously ranges from 30° C. to 90° C., more preferably from 40° C. to 75° C.

The process of the invention is advantageously carried out at a pressure ranging from 0.5 to 10 bar, more preferably at a pressure which is close to atmospheric pressure.

The contact time typically ranges from 10 minutes to 2 hours.

The nitrocresol destruction according to the invention can be carried out equally as well in one or in several successive steps.

Downstream of the contacting step, the mixture is decanted and the organic phase is separated from the aqueous phase.

The organic phase thus separated can then be washed with water.

This operation is carried out conventionally, with stirring, at a temperature of from 20° C. to 90° C. and for a period of time ranging from several minutes to two hours.

The mixture is then decanted and the organic phase, containing the purified nitroaromatic compounds, is separated from the aqueous phase.

It will also be appreciated that the process of the invention can advantageously be carried out either in continuous or batch mode.

In the latter event, for obvious reasons of economy, one and/or the other of the two agents should be recycled.

The present invention also features the use of the purified nitroaromatic compounds for the production of aromatic diamines.

In general, this reaction comprises a reduction of the nitro groups to amine groups.

The nitroaromatic compounds, if necessary following a drying step using any known means, are reacted with pure or diluted hydrogen in the presence of a conventional hydrogenation catalyst, for example Raney nickel or a platinum based catalyst.

The reaction temperature normally ranges from 100° C. to 200° C. and the pressure during the reaction generally ranges from 1 to 150 bar.

In order to further illustrate the present invention and the advantages thereof, the following specific examples are given, it being understood that same are intended only as illustrative and in nowise limitative.

EXAMPLE 1 (Comparative)

Toluene was reacted with nitric acid in the presence of sulfuric acid. The resulting mixture was washed with water to eliminate the mineral acids. The mixture was decanted and the organic phase, containing the nitrotoluenes to be purified and about 500 ppm of nitrocresols, was recovered.

10 g of toluene were then added to 10.6 g of the resulting mixture.

20 ml of water, then a 36% aqueous sodium hydroxide solution, were introduced with stirring to adjust the pH of the aqueous phase to about 7.

The mixture obtained was stirred for 2 hours at a temperature of 70° C.

The mixture was then decanted to provide a pale yellow organic phase and a bright red aqueous phase.

The composition and nitrocresol content in each of the two phases were analyzed via liquid phase chromatography.

The results obtained are reported in the following Table 1:

TABLE 1

| | Residual nitrocresol content | | |
|---|---|---|---|
| | (1), % | (2), % | (3), % |
| Aqueous phase | 87 | 98 | 100 |
| Organic phase | 13 | 2 | 0 |
| Destruction ratio | 0 | 0 | 0 |

(1) 2,4,6-metatrinitrocresol
(2) 3,4,6-orthotrinitrocresol
(3) 2,3,6-paratrinitrocresol The overall nitrocresol destruction ratio was zero.

EXAMPLE 2

Toluene was reacted with nitric acid in the presence of sulfuric acid. The resulting mixture was washed with water to eliminate the mineral acids. The mixture was decanted and the organic phase, containing the nitrotoluenes to be purified and about 500 ppm of nitrocresols, was recovered.

10 g of toluene were then added to 10 g of the resulting mixture.

20 ml of an aqueous 10% solution of hydrogen peroxide were introduced with stirring.

A 36% aqueous sodium hydroxide solution was then added in such amount as to adjust the pH of the aqueous phase to a value of about 7.

The mixture obtained was stirred for 2 hours at a temperature of 70° C.

The mixture was decanted to provide two pale yellow phases.

The composition and nitrocresol content in each of the two phases were analyzed via liquid phase chromatography.

The results obtained are reported in the following Table 2:

TABLE 2

| | Residual nitrocresol content | | |
|---|---|---|---|
| | (1), % | (2), % | (3), % |
| Aqueous phase | 36 | 0 | 0 |
| Organic phase | 4 | 2.5 | 0 |
| Destruction ratio | 60 | 97.5 | 100 |

(1) 2,4,6-metatrinitrocresol
(2) 3,4,6-orthotrinitrocresol
(3) 2,3,6-paratrinitrocresol The overall trinitrocresol destruction ratio was 86%.

The amount of dinitrotoluenes in the organic phase determined by gas phase chromatography, was identical to that determined in Example 1 (with respect to the same initial amount of dinitrotoluenes).

EXAMPLE 3

Toluene was reacted with nitric acid in the presence of sulfuric acid. The resulting mixture was washed with water to eliminate the mineral acids. The mixture was decanted and the organic phase, containing the nitrotoluenes to be purified and about 500 ppm of nitrocresols, was recovered.

10 g of toluene were then added to 10 g of the resulting mixture.

20 ml of an aqueous 10% solution of hydrogen peroxide were introduced with stirring.

Sulfuric acid was then added in such amount as to a just the pH of the aqueous phase to a value of about 1.

The mixture obtained was stirred for 2 hours at a temperature of 70° C.

The mixture was decanted to provide two pale yellow phases.

The composition and nitrocresol content in each of the two phases were analyzed via liquid phase chromatography.

The results obtained are reported in the following Table 3:

TABLE 3

| | Residual nitrocresol content | | |
|---|---|---|---|
| | (1), % | (2), % | (3), % |
| Aqueous phase | 29 | 0 | 0 |
| Organic phase | 7 | 1 | 0 |
| Destruction ratio | 63 | 99 | 100 |

(1) 2,4,6-metatrinitrocresol
(2) 3,4,6-orthotrinitrocresol
(3) 2,3,6-paratrinitrocresol The overall trinitrocresol destruction ratio was 87%.

The amount of dinitrotoluenes in the organic phase, determined by gas phase chromatography, was identical to that determined in Example 1 (with respect to the same initial amount of dinitrotoluenes).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the removal of hydroxynitroaromatic compound impurities from an admixture having nitroaromatic compounds with two nitro groups as major components thereof, which comprises:

first intimately contacting such nitroaromatic admixture including the hydroxynitroaromatic compound impurities with an oxidizing agent comprising hydrogen peroxide, javelle water, or a mixture thereof, and thereafter with a neutralizing agent.

2. The process as defined by claim 1, said nitroaromatic compound admixture comprising the medium of nitration of an aromatic compound by reacting same with aqueous nitric acid, in the presence of sulfuric acid.

3. The process as defined by claim 2, said oxidizing agent comprising hydrogen peroxide.

4. The process as defined by claim 3, said neutralizing agent comprising an alkali or alkaline earth metal hydroxide, carbonate, bicarbonate, or mixture thereof.

5. The process as defined by claim 4, said neutralizing agent comprising an alkali metal hydroxide.

6. The process as defined by claim 1, the amount of said oxidizing agent being from about 15 to about 1,000 moles thereof per mole of hydroxynitroaromatic, which is nitrocresol in said admixture.

7. The process as defined by claim 6, said amount of oxidizing agent ranging from 15 to 500 moles thereof per mole of nitrocresol.

8. The process as defined by claim 1, said oxidizing agent comprising an up to 50% solvent solution thereof.

9. The process as defined by claim 1, said neutralizing agent comprising an up to 50% solvent solution thereof.

10. The process as defined by claim 1, the medium of neutralization comprising an aqueous phase having a pH ranging from 1 to 9.

11. The process as defined by claim 1, said admixture of nitroaromatic compounds comprising up to 1,000 ppm of nitrocresols.

12. The process as defined by claim 1, comprising neutralizing said nitrocresol values into water soluble salts thereof.

13. The process as defined by claim 1, wherein said admixture corresponds to the organic phase obtained after separation from an inorganic nitrating medium after a process of nitration of aromatic compounds.

14. The process as defined by claim 13, wherein said nitrating medium is a nitric acid in the presence of sulfuric acid.

15. A process for removing hydroxynitroaromatic compound impurities from an admixture having nitroaromatic compounds with two nitro groups as major components thereof after a process of nitration of aromatic compounds with an inorganic nitrating medium of nitric acid in the presence of sulfuric acid comprising steps of:

a) separating the nitrating medium into an aqueous phase and an organic, nitroaromatic admixture phase including the hydroxynitroaromatic compound impurities, b) intimately contacting said nitroaromatic admixture with an oxidizing agent comprising hydrogen peroxide, javelle water, or a mixture thereof, and c) thereafter contacting said admixture with a neutralizing agent.

16. The process as defined in claim 15 comprising the additional step of washing said organic, nitroaromatic admixture phase-with water after step a and prior to step b.

17. The process as defined in claim 15 comprising the additional step, after step c, of washing said admixture after contacting it with a neutralizing agent.

18. The process as defined in claim 15 comprising the additional step of adding a cosolvent to said organic, nitroaromatic admixture phase prior to step a.

* * * * *